(12) United States Patent
Kropf et al.

(10) Patent No.: US 9,006,168 B2
(45) Date of Patent: Apr. 14, 2015

(54) ODORANT COMPOSITION CONTAINING ALLYL ETHERS AS ODORANT PRECURSORS

(71) Applicant: Henkel AG & Co. KGaA, Duesseldorf (DE)

(72) Inventors: Christian Kropf, Hilden (DE); Thomas Gerke, Duesseldorf (DE); Ursula Huchel, Cologne (DE); Thomas J. J. Mueller, Duesseldorf (DE); Jan Nordmann, Dormagen (DE)

(73) Assignee: Henkel AG & Co., KGaA, Duesseldorf (DE)

( * ) Notice: Subject to any disclaimer, the term of this patent is extended or adjusted under 35 U.S.C. 154(b) by 0 days.

(21) Appl. No.: 14/039,001

(22) Filed: Sep. 27, 2013

(65) Prior Publication Data

US 2014/0030397 A1 Jan. 30, 2014

Related U.S. Application Data

(63) Continuation of application No. PCT/EP2012/055158, filed on Mar. 23, 2012.

(30) Foreign Application Priority Data

Mar. 29, 2011 (DE) .................. 10 2011 006 314

(51) Int. Cl.
| | |
|---|---|
| *A61K 8/00* | (2006.01) |
| *C07C 69/608* | (2006.01) |
| *A23L 1/226* | (2006.01) |
| *C11B 9/00* | (2006.01) |
| *C11D 3/50* | (2006.01) |
| *A61K 8/35* | (2006.01) |
| *A61Q 13/00* | (2006.01) |

(52) U.S. Cl.
CPC ........... *C07C 69/608* (2013.01); *A23L 1/22607* (2013.01); *C11B 9/0003* (2013.01); *C11D 3/507* (2013.01); *A61K 8/35* (2013.01); *A61Q 13/00* (2013.01); *A23L 1/2265* (2013.01)

(58) Field of Classification Search
USPC .............................................. 512/1; 568/687
See application file for complete search history.

(56) References Cited

U.S. PATENT DOCUMENTS

| | | | |
|---|---|---|---|
| 4,150,000 A | | 4/1979 | Dastur et al. |
| 4,241,098 A | * | 12/1980 | Mussinan et al. ............. 426/534 |
| 4,601,851 A | | 7/1986 | Bartmann et al. |
| 4,902,672 A | | 2/1990 | Sprecker et al. |
| 5,649,979 A | * | 7/1997 | Paget et al. ........................ 8/137 |
| 6,340,666 B1 | | 1/2002 | Narula et al. |
| 8,129,569 B2 | | 3/2012 | Huchel et al. |
| 2008/0305063 A1 | | 12/2008 | Huchel et al. |

FOREIGN PATENT DOCUMENTS

DE 19841147 A1 3/2000

OTHER PUBLICATIONS

PCT International Search Report (PCT/EP2012/055158) dated Apr. 6, 2012.
Wennerberg et al., "Zeolite B Induced Rearrangement of Allyl Benzyl Ethers. 6. Variation of the Aromatic Part and Synthesis of Dihydronaphthalene Derivatives", Journal of Organic Chemistry, vol. 64, pp. 54-59, 1999.
Kwart et al., "Mechanisms of Thermolytic Fragmentation of Allyl Ethers", Journal of the American Chemical Society, vol. 95(16), pp. 5234-5242, 1973.

* cited by examiner

*Primary Examiner* — John Hardee
(74) *Attorney, Agent, or Firm* — Thomas G. Krivulka

(57) ABSTRACT

The deliberate release of odorants or aroma substances is desirable in many fields of application, and in particular in the field of washing and cleaning agents. Said deliberate release is achieved by using an odorant composition that comprises an odorant precursor, which is an allyl ether of the formula (I), $R^1R^2C=CR^3-CR^4R^5-O-CHR^6R^7$, in which the residues $R^1$, $R^2$, $R^3$, $R^4$, $R^5$, $R^6$ and $R^7$ mutually independently denote H or a hydrocarbon residue that can be acyclic or cyclic, substituted or unsubstituted, branched or unbranched, as well as saturated or unsaturated. Thus, in particular odorants in the form of an alkene having an allylic hydrogen atom, such as α-pinene, can be released in a deliberate manner.

6 Claims, No Drawings

ODORANT COMPOSITION CONTAINING ALLYL ETHERS AS ODORANT PRECURSORS

FIELD OF THE INVENTION

The present invention generally relates to odorant precursors which enable the release of odorants, and more particularly relates to allyl ether-based precursor compounds. The invention furthermore relates to the use of corresponding odorant precursors in odorant compositions and in perfumed or aromatized consumer products, such as for example washing or cleaning agents. It furthermore relates to textile fragrancing methods and aromatization methods in foodstuff preparation.

BACKGROUND OF THE INVENTION

The principle underlying the function of odorant precursor compounds is fundamentally known. It generally involves converting odorants into compounds which do not bring about a direct scent or aroma impression but which, in response to a specific stimulus, for example on exposure to heat or acid, are capable of releasing the original odorant and thus obtain a scenting or aroma action. The intention here is to protect the odorant until it is released in targeted manner.

Known odorant precursors are for example silicic acid esters. Such compounds are described in German published patent application DE 198 41 147 A1. These silicic acid esters contain residues of scent alcohols, such as for example octan-1-ol, and are suitable for fragrancing washing and cleaning agents since they release the alcohols with a scenting action on hydrolysis.

Oxazolidine-based odorant precursors are furthermore known. Such compounds are described in German published patent application DE 10 2006 003 092 A1. The odorant precursors described therein are bicyclic oxazolidine derivatives of scent ketones or aldehydes, such as for example decanal, which are capable of releasing the aldehydes or ketones with a scenting action on hydrolysis.

Photolabile odorant precursors are also known, which enable photoinduced release of odorants. Such compounds are described in German published patent application DE 10 2008 016 327 A1. The systems described therein are specific ketones which enable the release of terpenoids or terpenes with a scenting action, such as for example β-phellandrene, after exposure to electromagnetic radiation including the wavelengths from 200 to 400 nm.

In J. Org. Chem. 1999, 64, 54-59, J. Wennerberg et al. describe catalysts for the retro-ene reaction-related rearrangement of benzyl allyl ethers. In J. Am. Chem. Soc, 1973, 95, 5234-5242, H. Kwart et al. describe the thermally induced reaction of allyl ethers. However, neither odorant compositions nor washing or cleaning agents are described therein.

Against this background, it was the object of the present invention to provide further compositions which enable targeted odorant release.

Said object is achieved by the subject matter of the invention, namely an odorant composition, containing an odorant precursor, which is an allyl ether of the formula (I), $$R^1R^2C=CR^3-CR^4R^5-O-CHR^6R^7 \quad (I),$$

in which the residues $R^1$, $R^2$, $R^3$, $R^4$, $R^5$, $R^6$ and $R^7$ mutually independently in each case denote H or a hydrocarbon residue that can be acyclic or cyclic, substituted or unsubstituted, branched or unbranched, as well as saturated or unsaturated, and in which individual residues $R^1$, $R^2$, $R^3$, $R^4$, $R^5$, $R^6$, $R^7$ can form a ring system with one another, wherein $R^1$, $R^2$, $R^3$, $R^4$ and $R^5$ denote residues that, in a compound of the general formula (II)

$$R^1R^2CH-CR^3=CR^4R^5 \quad (II)$$

give rise to an odorant, in which the residue $R^3$ can form a ring system with one of residues $R^1$ or $R^5$, and/or wherein $R^6$ and $R^7$ denote residues that, in a compound of the general formula (III)

$$R^6R^7C=O \quad (III)$$

give rise to an odorant, in which residues $R^6$ and $R^7$ can preferably form a ring system. The respective hydrocarbon residues may advantageously in each case comprise 1 to preferably 15 carbon atoms.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An odorant composition, containing an odorant precursor, which is an allyl ether of the formula (I), $$R^1R^2C=CR^3-CR^4R^5-O-CHR^6R^7 \quad (I),$$

in which the residues $R^1$, $R^2$, $R^3$, $R^4$, $R^5$, $R^6$ and $R^7$ mutually independently in each case denote H or a hydrocarbon residue that can be acyclic or cyclic, substituted or unsubstituted, branched or unbranched, as well as saturated or unsaturated, and in which individual residues $R^1$, $R^2$, $R^3$, $R^4$, $R^5$, $R^6$, $R^7$ can form a ring system with one another, wherein $R^1$, $R^2$, $R^3$, $R^4$ and $R^5$ denote residues that, in a compound of the general formula (II)

$$R^1R^2CH-CR^3=CR^4R^5 \quad (II),$$

give rise to an odorant, and/or wherein $R^6$ and $R^7$ denote residues that, in a compound of the general formula (III)

$$R^6R^7C=O \quad (III),$$

give rise to an odorant.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It is possible according to the invention for individual residues $R^1$, $R^2$, $R^3$, $R^4$, $R^5$, $R^6$, $R^7$ to form a ring system with one another. These may comprise both monocyclic and bicyclic ring systems. For example, the residue $R^3$ can form a ring system, in particular a bicyclic ring system, both with the residue $R^1$ and with the residue $R^5$. Examples of such odorant precursors with ring formation between the residues which for the purposes of the present invention comply with formula (I) are for example myrtenol ethers, such as for example

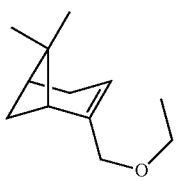

or for example pinocarveol ethers, such as for example

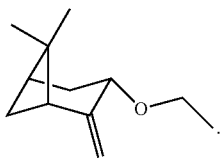

A bicyclic ring system is here present in each case. Myrtenol ethers, pinocarveol ethers and para-mentha-1,4(8)-dien-9-ol ethers are particularly preferred odorant precursors for the purposes of the invention.

It is also possible for residue $R^6$ to form a ring system with residue $R^7$. The following two compounds are examples of this:

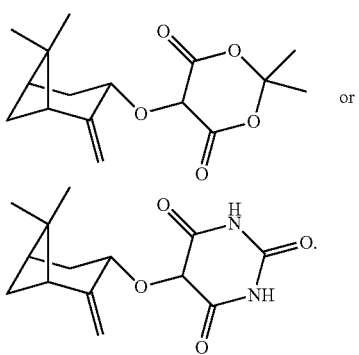

In this case, residues $R^6$ and $R^7$ in each case form a monocyclic ring system.

Further examples of odorant precursors for the purposes of the invention are the following compounds:

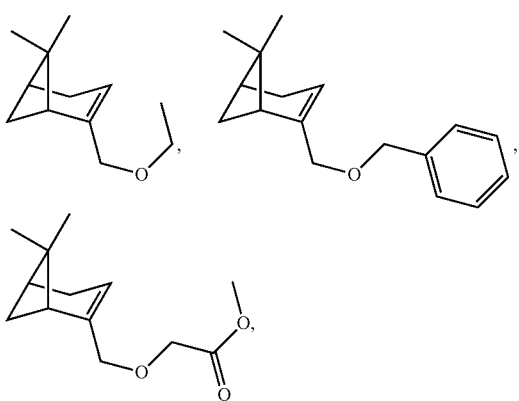

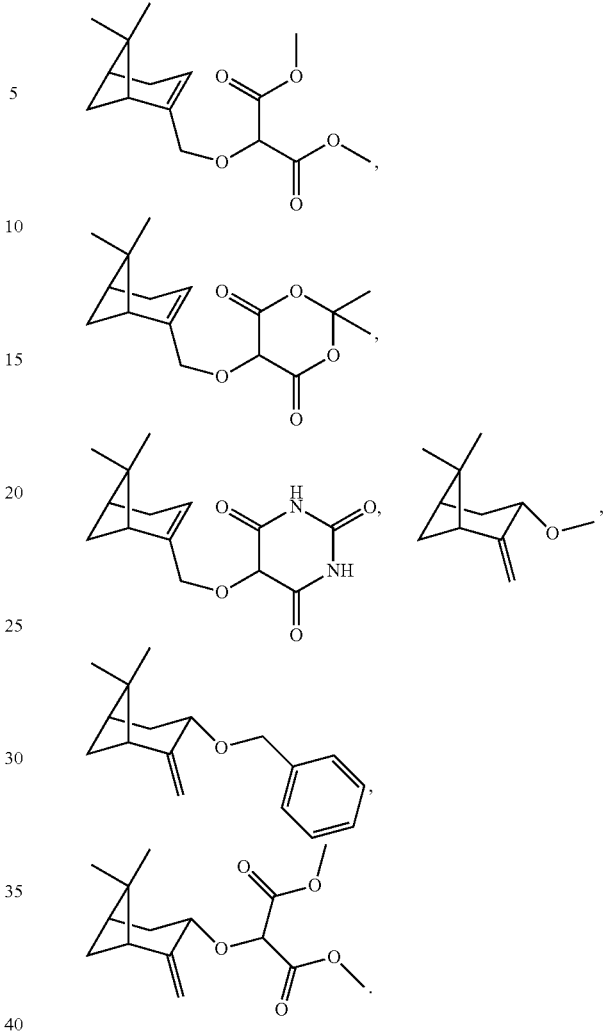

The odorant precursors according to the invention may in principle be prepared using the Williamson ether synthesis. For example, p-methoxybenzyl allyl ether is obtainable by the corresponding reaction of anisyl alcohol with allyl bromide using sodium hydride as base in THF. The octyl allyl ether is obtainable by the corresponding reaction of 1-octanol with allyl bromide using sodium hydride as base in THF. Myrtenol methyl ether is obtainable by the corresponding reaction of myrtenol with iodomethane and sodium hydride as base in THF. The examples section furthermore describes the preparation of trans-pinocarvyl oxyacetic acid methyl ester.

"Odorant composition" is the name for a composition which comprises at least one odorant precursor, but generally a plurality of further odorants (for example more than 5, more than 10 or more than 20 different odorants). The odorant composition according to the invention thus contains at least one odorant precursor compound according to formula (I). The odorant composition according to the invention may, in addition to the odorant precursor compound according to formula (I), contain one or more further odorants.

"Odorants" is the name for chemical compounds with an odor which in humans trigger a preferably pleasant odor sensation (scents) and are therefore conventionally used for perfuming or fragrancing industrial and sanitary articles, soaps, personal hygiene products, washing agents, cleaning agents and the like. The terms odorants and scents should be taken to be synonymous. For the purposes of the present invention, the term odorants is taken to include "aroma substances". Aroma substances is the term used to designate substances with an odor action in foodstuffs. "Aroma substances" in foodstuffs are perceived not only by being drawn in through the nose, i.e. orthonasally, but also via the pharynx after or during chewing or drinking, i.e. retronasally. Aroma substances are generally added to foodstuffs in order to impart a particular odor or flavor thereto or to improve or modify, for example enhance, an existing odor or flavor. Together with the nonvolatile flavors (i.e. compounds with a sour, sweet, bitter, salty or spicy hot flavor), aroma substances thus make a vital contribution to the aroma of a foodstuff. Ethyl vanillin, for example, is an important aroma substance because it has a much more intense vanilla-like aroma than vanillin. Ethyl vanillin is therefore frequently used as an aroma substance in foodstuffs, beverages and also feedstuffs. Ethyl vanillin is, however, also likewise successfully used as a common odorant (scent) in conventional perfume and cosmetic compositions. Preferred odorants will also be mentioned in the course of the description. Since, for the purposes of the present invention, the term odorants also encompasses "aroma substances", the same also applies mutatis mutandis to the terms "aroma substance composition" and "odorant composition". For the purposes of the invention, the term "odorant composition" thus also encompasses the term "aroma substance composition" and perfume. An "aroma substance composition" for the purposes of the invention is a specific odorant composition which is suitable for use in foodstuffs and thus for consumption. Perfumes are taken to mean alcoholic solutions suitable odorants (scents). It goes without saying that an "odorant composition" according to the invention may, in addition to the odorants and the odorant precursor according to the invention present therein, also contain further typical ingredients, such as for example solvents or the like.

The precursor compounds of the general formula (I) used according to the invention enable the targeted release of aldehydes or ketones with a scenting action and/or odorants with an allylic hydrogen atom. Release may here in particular be induced thermally and/or by acid catalysis, the precursor compound of formula (I) dissociating into compounds of the general formula (II) and of the general formula (III) in accordance with the "retro-ene reaction". The retro-ene reaction is known per se and involves the reversal of the ene reaction. The ene reaction is taken to mean the addition investigated by Kurt Alder of alkenes with allylic hydrogen atoms onto "enophiles", i.e. H acceptors. Enophiles are here not restricted to the group of alkenes. Alkynes or groups bearing heteroatoms which have a multiple bond may also be used. If carbonyls are involved, the reaction is also known as a carbonyl ene reaction. In this respect, the precursor compound of formula (I) dissociates in accordance with a reaction which is a reversal of the carbonyl ene reaction, to form a carbonyl compound (aldehyde or ketone) of formula (III), which corresponds to the enophile, and an alkene with an allylic hydrogen atom according to formula (II).

According to the invention, at least one of the compounds of formula (II) or (III) arising from the dissociation of the precursor compound according to formula (I) is an odorant. It is also possible for both dissociation compounds to be odorants. It is, however, particularly preferred for dissociation of the precursor compound to give rise to an odorant in the form of an alkene with an allylic hydrogen atom according to formula (II).

The present invention thus enables the targeted release of aldehydes or ketones with a scenting action (aldehydes or ketones with a scenting action within the meaning of odorants) and/or odorants or aroma substances with an allylic hydrogen atom. Release may in particular be induced thermally, for example when using a tumble dryer, on ironing or during machine washing preferably at elevated temperature.

Release may also be induced by acid catalysis, such that the present invention also enables delayed release of aldehydes or ketones with a scenting action and/or odorants or aroma substances with an allylic hydrogen atom by pH change, for example by reducing the pH in the rinse cycle or gradually on dry laundry due to contact with the constantly weakly acidic ambient humidity.

The two release mechanisms, which may if desired also be combined, can bring about a targeted "scent boost" (production of a strong scent impression), for example during ironing. An extended scent action may likewise also be achieved.

In connection with foodstuffs and the preparation thereof, the present invention enables the targeted release of aroma substance aldehydes or ketones and/or alkenes on exposure to a thermal stimulus, for example on boiling, frying or baking.

Preferred examples of allyl ethers which are usable according to the invention are for example benzyl allyl ethers and the derivatives thereof, such as for example p-methoxybenzyl allyl ether.

Likewise preferred examples of allyl ethers which are usable according to the invention are for example alkyl or alkenyl allyl ethers, such as for example n-octyl allyl ether, n-heptyl allyl ether, n-nonyl allyl ether, n-decyl allyl ether, 2-undecyl allyl ether or 2-heptyl-6-methyl-5-enyl allyl ether.

According to a preferred embodiment, the residue $R^6$ in the formula (I) thus denotes hydrogen and residue $R^7$ denotes an alkyl or alkenyl residue with at least 7 carbon atoms or denotes an optionally substituted phenyl residue.

According to a preferred embodiment of the invention, residues $R^2$ and $R^4$ in formula (I) are hydrogen residues (precursor compound thus corresponds to: $R^1CH=CR^3-CHR^5-O-CHR^6R^7$), wherein $R^1$, $R^3$ and $R^5$ denote residues that, in a compound of the general formula (IV)

give rise to an odorant, in which the residue $R^3$ can form a ring system with one of residues $R^1$ or $R^5$,
and/or wherein $R^6$ and $R^7$ denote residues that, in a compound of the general formula (III)

give rise to an odorant. For the purposes of a preferred embodiment, residue $R^3$ forms a ring system either with residue $R^1$ or alternatively with residue $R^5$ and/or residue $R^6$ forms a ring system with residue $R^7$.

According to a further preferred embodiment of the invention, residues $R^2$, $R^4$ and $R^6$ in formula (I) are hydrogen residues (precursor compound thus corresponds to:

wherein $R^1$, $R^3$ and $R^5$ denote residues that, in a compound of the general formula (IV)

give rise to an odorant, in which the residue $R^3$ can form a ring system with one of residues $R^1$ or $R^5$,
and/or wherein $R^7$ denotes a residue that, in a compound of the general formula (V)

gives rise to an odorant. For the purposes of a preferred embodiment, residue $R^3$ forms a ring system either with residue $R^1$ or alternatively with residue $R^5$.

According to a further preferred embodiment of the invention, residues $R^2$, $R^4$, $R^5$ and $R^6$ in formula (I) are hydrogen residues (precursor compound thus corresponds to:

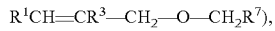

wherein $R^1$ and $R^3$ denote residues that; in a compound of the general formula (VI)

 (VI)

give rise to an odorant, in which residue $R^3$ can preferably form a ring system with residue $R^1$,
and/or wherein $R^7$ denotes a residue that, in a compound of the general formula (V)

 (V)

gives rise to an odorant. One example of such a precursor compound is the following myrtenol ether

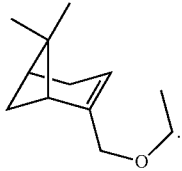

In this example, residues $R^2$, $R^4$, $R^5$ and $R^6$ are hydrogen residues. Residues $R^1$ and $R^3$ are connected together and form a ring system. Residue $R^7$ corresponds to the $CH_3$ grouping.

According to a further preferred embodiment of the invention, residues $R^1$, $R^2$, $R^4$ and $R^6$ in formula (I) are hydrogen residues (precursor compound thus corresponds to:

wherein $R^3$ and $R^5$ denote residues that, in a compound of the general formula (VI)

 (VI)

give rise to an odorant, in which residues $R^3$ and $R^5$ can preferably also form a ring system, and/or wherein $R^7$ denotes a residue that, in a compound of the general formula (V)

 (V)

gives rise to an odorant. One example of such a precursor compound is pinocarvyl oxyacetic acid methyl ester:

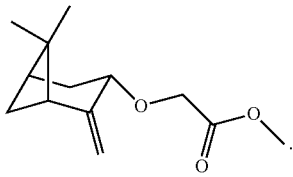 [SMILES: C=C1C(OCC(=O)OC)CC2CC1C2(C)C]

In this example, residues $R^1$, $R^2$, $R^4$ and $R^6$ are hydrogen residues. Residues $R^3$ and $R^5$ are connected together and form a ring system. Residue $R^7$ corresponds the COO-Me grouping.

While it is indeed particularly preferred for dissociation of the precursor compound to give rise to an odorant in the form of an alkene with an allylic hydrogen atom according to formula (II), the present invention nevertheless also enables the release of carbonyl compounds with a scenting action, in particular odorant aldehydes.

It is therefore a further preferred embodiment of the invention for the compound of the general formula (III) or (V) to be an odorant aldehyde, in particular selected from adoxal (2,6,10-trimethyl-9-undecenal), anisaldehyde (4-methoxybenzaldehyde), cymal (3-(4-isopropylphenyl)-2-methylpropanal), ethylvanillin, florhydral (3-(3-isopropylphenyl)butanal), helional (3-(3,4-methylenedioxyphenyl)-2-methylpropanal), heliotropin, hydroxycitronellal, lauraldehyde, lyral (3- and 4-(4-hydroxy-4-methylpentyl)-3-cyclohexene-1-carboxaldehyde), methylnonylacetaldehyde, lilial (3-(4-tert.-butylphenyl)-2-methylpropanal), phenylacetaldehyde, undecylenealdehyde, vanillin, 2,6,10-trimethyl-9-undecenal, 3-dodecen-1-al, alpha-n-amylcinnamaldehyde, melonal (2,6-dimethyl-5-heptenal), 2,4-dimethyl-3-cyclohexene-1-carboxaldehyde (triplal), benzaldehyde, 3-(4-tert.-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, 2,6-dimethyl-5-heptenal, 4-(tricyclo[5.2.1.0(2,6)]-decylidene-8)-butanal, octahydro-4,7-methane-1H-indenecarboxaldehyde, 3-ethoxy-4-hydroxybenzaldehyde, para-ethyl-alpha, alpha-dimethylhydrocinnamaldehyde, alpha-methyl-3,4-(methylenedioxy)-hydrocinnamaldehyde, 3,4-methylenedioxybenzaldehyde, alpha-n-hexylcinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexane-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert.-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methanindane-1- or -2-carboxaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxaldehyde, 7-hydroxy-3,7-dimethyloctanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanindane-1-carboxaldehyde, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]hept-5-ene-2-carbaldehyde, 9-decenal, 3-methyl-5-phenyl-1-pentanal, methylnonylacetaldehyde, hexanal and trans-2-hexenal.

With regard to further suitable odorants selected from aldehydes, reference is made to Steffen Arctander Published 1960 and 1969 respectively, Reprinted 2000 ISBN: Aroma Chemicals Vol. 1: 0-931710-37-5, Aroma Chemicals Vol. 2:

0-931710-38-3. Suitable odorants selected from ketones are likewise to be found in said literature reference.

According to a further preferred embodiment of the invention, the alkene according to formula (II), (IV) or (VI) is selected from odorants or aroma substances with an allylic hydrogen atom, in particular from limonene, α-phellandrene, β-phellandrene, α-pinene, β-pinene, camphene, caryophyllene, longifolene, ocimene; α-terpinene, β-terpinene, γ-terpinene, α-terpineol, δ-terpineol, γ-terpineol, β-terpineol, α-citronellol, β-citronellol, α-citronellal, β-citronellal, linalool, geraniol, santalol, hasmigone, carvone, 2-carene, 3-carene, 4-carene, elemol and/or curcumene. Particularly preferred alkenes according to formula (II), (IV) or (VI) are those which are true hydrocarbons, i.e. compounds solely consisting of carbon (C) and hydrogen (H), such as for example pinene or terpinene. Further suitable odorants with an allylic hydrogen atom may be found in the above-stated literature reference, Steffen Arctander.

Release of the odorants or aroma substances from the precursor compound is in particular induced by input of heat and/or by acid catalysis, in which the use of Brønsted acids is preferred, but the use of Lewis acids is possible. The acids may be used in catalytic quantities. In particular, input of heat in conjunction with the use of catalytic quantities of acids is preferred.

Odorant precursors which are particularly preferred for the purposes of the present invention are those according to formula (I) with ring formation between residues $R^6$ and $R^7$, since the activation energy for thermal cleavage is particularly low in these compounds.

The odorant precursors according to the invention are very highly suitable for incorporation into other compositions or agents, such as for example perfume or aroma substance compositions, washing agents etc. and enable targeted scent or aroma release during use of the agent. The odorant precursors can be stably incorporated into such agents. The resultant agents are stable in storage.

In addition to the precursor compound according to the invention, an odorant composition according to the invention preferably contains still further substances which are usual in perfumes or odorant or aroma substance compositions. These include in particular odorants or aroma substances and/or solvents.

According to a preferred embodiment of the invention, the odorant composition according to the invention contains at least one precursor compound according to the invention, as previously described, in quantities between 0.001 and 25 wt. %, preferably between 0.01 and 15 wt. %, more advantageously between 0.1 and 10 wt. %, in particular between 1 and 5 wt. %, in each case relative to the entire composition.

According to a particularly preferred embodiment of the invention, in addition to the precursor compound according to the invention, the odorant composition according to the invention contains additional odorants, for example in a quantity of 0.1 to 99 wt. %, preferably 5-90 wt. %, in particular 15-70 wt. %, relative to the entire odorant composition.

Typical auxiliary substances may likewise be present, such as for example antioxidants (collective term for compounds of various chemical structures which inhibit or prevent unwanted changes in the compositions to be protected brought about by the action of oxygen and other oxidative processes), preservatives (collective term for compounds of various chemical structures which inhibit or prevent unwanted changes in the compositions to be protected brought about by the action of microorganisms) or for example fixatives.

Fixatives, which are optionally usable as auxiliary substances, are substances which are capable of imparting elevated stability to odorants. Particularly suitable fixatives are "intrinsic" fixatives which, thanks to their low volatility retain their intrinsic odor for an extended period without in so doing impeding other more highly volatile components from emitting their odor, such as in particular synthetic musks, together with "pseudofixatives" as substances with a slight odor, such as for example diethylene glycol methyl ether, and furthermore those fixatives which fix by adsorption forces, such as in particular extracts of labdanum, styrax, tolu balsam, benzoin, iris, oak moss or opopanax etc.

Suitable optional solvents which may preferably be present in an odorant composition according to the invention are those conventional in perfumery, such as preferably dipropylene glycol, diethylene glycol, isopropyl myristate, ethanol, water, propylene glycol and/or castor oil. Other suitable optional auxiliary substances are for example complexing agents.

According to a preferred embodiment of the invention, the odorant composition according to the invention contains solvents, for example in a quantity of 0.1 to 95 wt. %, preferably 5-90 wt. %, in particular 15-70 wt. %, relative to the odorant composition.

In particular in the case of a pulverulent odorant composition, said composition may also contain solid support materials as auxiliary substances. Suitable solid support materials are known to a person skilled in the art and are determined on the basis of the intended purpose of the composition. Usual solid support materials for aroma substances are for example maltodextrins, since they are virtually flavor-neutral.

The odorant compositions according to the invention may in principle also contain surfactants as optional auxiliary substances. However, to the extent that any surfactants at all are present, it is particularly preferred for the odorant composition according to the invention to comprise <15 wt. %, preferably <5 wt. %, in particular <1 wt. % surfactants. The surfactant content may also be below 10 wt. % or below 3 wt. % or below 0.5 wt. %, below 0.1 wt. % or below 0.01 wt. %. If surfactants are present, which is optional, then a suitable minimum quantity may be for example 0.0001 wt. % or 0.001 wt. %, wt. % in each case relative to the entire composition. For the purposes of the invention, the term surfactants also includes emulsifiers as interfacially active substances. Preferably usable emulsifiers are ethoxylated fatty alcohols, ethoxylated triglycerides, sorbitan fatty acid esters, together with hydrogenated, ethoxylated castor oil.

According to a further preferred embodiment of the invention, the odorant composition according to the invention is liquid. It may in principle also be solid, this being a further preferred embodiment of the invention.

The further odorants which may optionally be present in the odorant composition according to the invention are not subject to any particular restriction. For instance, individual odorant compounds of natural or synthetic origin, for example of the ester, ether, aldehyde, ketone, alcohol and hydrocarbon type, may be used. Odorant compounds of the ester type are for example benzyl acetate, phenoxyethyl isobutyrate, p-tert.-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramat, melusat and jasmacyclat. Ethers include, for example, benzyl ethyl ether and ambroxan, aldehydes include, for example, linear alkanals with 8-18 C atoms, citral, citronellal, citronellyloxyacetaldehyde, cyclamen aldehyde (3-(4-propan-2-ylphenyl)butanal), lilial and bourgeonal, ketones include, for example, ionones, α-isomethylionone and methyl cedryl ketone, alcohols include anethole, citronellol, eugenol, geraniol, linalool, phenylethyl alcohol and terpineol, hydrocarbons mainly include terpenes such as limonene and pinene. Preferably, however, mixtures of various odorants are used which together produce an attractive scent note. The compositions according to the invention may also contain natural odorant mixtures, as are obtainable from plant sources, for example pine, citrus, jasmine, patchouli, rose or ylang-ylang oil. Likewise suitable are muscatel sage oil, chamomile oil, clove oil, melissa oil, mint oil, cinnamon leaf oil, lime blossom oil, juniper berry oil, vetiver oil, olibanum oil, galbanum oil and labdanum oil and orange-blossom oil, neroli oil, orange peel oil and sandalwood oil.

Further conventional odorants which may be present for the purposes of the present invention in the odorant compositions according to the invention, are for example essential oils such as angelica root oil, anise oil, arnica blossom oil, basil oil, bay oil, champak flower oil, silver fir oil, silver fir cone oil, elemi oil, eucalyptus oil, fennel oil, spruce-needle oil, galbanum oil, geranium oil, ginger grass oil, guaiacwood oil, gurjun balsam oil, helichrysum oil, ho oil, ginger oil, iris oil, cajeput oil, calamus oil, chamomile oil, camphor oil, canaga oil, cardamom oil, cassia oil, pine-needle oil, copaiba balsam oil, coriander oil, spearmint oil, caraway oil, cumin oil, lavender oil, lemongrass oil, lime oil, mandarin oil, melissa oil, ambrette oil, myrrh oil, clove oil, neroli oil, niaouli oil, olibanum oil, origanum oil, palmarosa oil, patchouli oil, Peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronellol, lemon oil and cypress oil, together with ambrettolide, ambroxan, α-amylcinnamaldehyde, anethole, anisaldehyde, anisyl alcohol, anisole, methyl anthranilate, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, Boisambrene Forte, α-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, methyl heptine carbonate, heptaldehyde, hydroquinone dimethyl ether, hydroxycinnamaldehyde, hydroxycinnamyl alcohol, indole, irane, isoeugenol, isoeugenol methyl ether, isosafrole, jasmone, camphor, carvacrol, carvone, p-cresol methyl ether, coumarin, p-methoxyacetophenone, methyl N-amyl ketone, methylanthranilic acid methyl ester, p-methylacetophenone, methylchavicol, p-methylquinoline, methyl β-naphthyl ketone, methyl n-nonylacetaldehyde, methyl n-nonyl ketone, muscone, β-naphthol ethyl ether, β-naphthol methyl ether, nerol, n-nonylaldehyde, nonyl alcohol, n-octylaldehyde, p-oxyacetophenone, pentadecanolide, β-phenylethyl alcohol, phenylacetic acid, pulegone, safrole, isoamyl salicylate, methyl salicylate, hexyl salicylate, cyclohexyl salicylate, santalol, sandelice, skatole, terpineol, thymene, thymol, troenan, γ-undecalactone, vanillin, veratrumaldehyde, cinnamaldehyde, cinnamyl alcohol, cinnamic acid, ethyl cinnamate, benzyl cinnamate, diphenyl oxide, limonene, linalool, linalyl acetate and propionate, melusate, menthol, menthone, methyl-n-heptenone, pinene, phenylacetaldehyde, terpinyl acetate, citral, citronellal and mixtures thereof.

According to one particularly preferred embodiment, the odorant composition according to the invention comprises, in addition to a precursor compound according to the invention, at least one odorant (scent), at least one solvent together with preferably at least one antioxidant. Particularly suitable odorants are those which are stored in the precursor compound according to the invention. It is thus a preferred embodiment for the odorant composition according to the invention moreover to contain, in addition to the precursor compound according to the invention, that or those odorant(s) which is/are stored in a precursor compound according to the invention.

As has already been explained, the odorant compositions according to the invention enable advantages in fragrancing consumer products, such as in particular washing or cleaning agents, since they enable scent advantages during use of the consumer products, in particular with regard to targeted scent or aroma release and with regard to gradual scent or aroma release. The odorant compositions according to the invention may be straightforwardly and stably incorporated into various consumer products such as in particular washing or cleaning agents, cosmetics, air fresheners or adhesives. Consumer products which are particularly preferred according to the invention are washing or cleaning agents. For the purposes of the present invention, the term washing or cleaning agents also includes laundry post-treatment agents such as in particular rinse conditioners, ironing aids or disinfectant rinses. Washing or cleaning agents are known per se to a person skilled in the art. Particularly preferred agents are solid, in particular pulverulent, washing agents, or liquid, in particular gel form, washing agents. The agents, such as in particular washing or cleaning agents, may also assume "pouch" form (i.e. in sachets), "sheet" form (i.e. wipes or films) or tablet form. The perfume compositions according to the invention may also be encapsulated prior to incorporation into the washing or cleaning agent.

The present invention also provides a perfumed or aromatized consumer product, in particular a washing or cleaning agent, laundry post-treatment agent, cosmetic agent, room fragrancing agent, foodstuff or adhesive, which contains a precursor compound according to the invention, as previously described. The respective consumer product furthermore advantageously contains the components conventional for the respective product. A person skilled in the art is in principle aware of such components or can find them in the relevant literature. It is particularly advantageous to use the perfume composition according to the invention in washing or cleaning agents.

The present invention accordingly also provides a washing or cleaning agent containing at least one odorant precursor according to the invention, as previously described, in quantities between 0.0001 and 10 wt. %, preferably between 0.001 and 5 wt. %, more advantageously between 0.01 and 3 wt. %, in particular between 0.1 and 2 wt. %, in each case relative to the entire agent. Such an agent furthermore contains the conventional components for washing or cleaning agents, such as for example surfactants, some of which are described in greater detail below.

When the washing or cleaning agent is used, the precursor compound may be deposited on the textile for example during washing. Scent may then be released from the precursor compound, for example during ironing. The temperature of the sole plate of a conventional iron may be set in conventional models to above 200° C., for example to approx. 220° C., whereby release of the desired odorants may be induced. It is likewise possible for the precursor compound already to dissociate in the washing liquor, in particular if washing is performed at elevated temperature, for example at ≥60° C. or at 95° C.

A washing or cleaning agent which is particularly preferred for the purposes of the invention is a laundry post-treatment agent, preferably a rinse conditioner, disinfectant rinse, dryer sheet, textile freshener or ironing aid, containing at least one odorant precursor as previously described, in quantities between 0.0001 and 10 wt. %, preferably between 0.001 and 5 wt. %, more advantageously between 0.01 and 3 wt. %, in particular between 0.1 and 2 wt. %, in each case relative to the entire agent. Such agents also furthermore contain the components conventional for the product category in question. For example, a disinfectant rinse conventionally contains active substances which, depending on the individual case, are capable of killing a wide range of viral, bacterial and fungal organisms. Such active substances, such as for example alkylbenzyldimethylammonium chloride, are known per se to a person skilled in the art. Rinse conditioners for example contain softening active substances, generally cationic surfactants, preferably ester quats, i.e. quaternary ammonium compounds with two hydrophobic residues, each of which contains an ester group as a "predetermined breaking point" to facilitate biodegradation.

The odorant compositions according to the invention and washing or cleaning agents according to the invention, such as in particular laundry post-treatment agents, have proven particularly advantageous in fragrancing textiles.

The present invention thus also provides a textile fragrancing method in which at least one odorant precursor according to the invention is applied onto a textile and the surface of the textile is thereafter exposed to temperatures of ≥50° C., preferably temperatures between 60° C. and 250° C., in particular in the presence of acids, preferably Brønsted acids. The temperature to which the surface of the textile is exposed for release of the odorant from the precursor compound may also amount to at least 80° C. or at least 95° C. In connection with release of the odorant during ironing, the temperature may also be ≥120° C., ≥150° C. or ≥200° C.

The odorant precursor may be applied for example during conventional textile washing, during which the odorant precursors are deposited on the textile. The textile may, however, as for example in the case of applying ironing aid, simply be sprayed with the composition in question.

It is likewise possible for cleavage of the odorant precursor and thus release of the bound odorants to occur already during textile washing, preferably in an automatic washing machine, release being induced by input of heat and/or by acid catalysis.

The present invention thus also provides a textile washing method in which the washing liquor contains at least one odorant precursor according to the invention and in which the temperature of the washing liquor in the course of the washing method is adjusted to ≥60° C., preferably to 80° C., in particular to 95° C.

The present invention likewise also provides a textile washing method in which the washing liquor contains at least one odorant precursor according to the invention and in which the temperature of the washing liquor in the course of the washing method amounts to ≤40° C., preferably ≤30° C. and in particular ≤20° C. Such a textile washing method enables deposition of the odorant precursor according to the invention onto the laundry, such that the bound odorants can be released when the laundry is post-treated, for example during ironing or use of an automatic tumble dryer.

The present invention also provides a textile fragrancing method in which moist textiles are introduced together with at least one odorant precursor according to the invention into an automatic tumble dryer and, in the course of the automatic tumble drying, the temperature in drying chamber is adjusted to ≥60° C., preferably to 80° C., in particular to 95° C. The odorant precursor may here for example already have been deposited on the moist textile by pretreatment or the odorant precursor may for example be introduced into the tumble dryer by means of a dryer sheet.

The present invention also provides a textile fragrancing method in which an odorant precursor according to the invention is applied onto a textile and thereafter the pH of the textile or of the medium surrounding the textile is adjusted to less than 7, preferably less than 5. This method involves gradual cleavage of the precursor compound deposited on the textile due to the constantly acidic ambient air.

The present invention also provides an aromatization method in foodstuff preparation in which a foodstuff (for example a dough prepared from ground cereal products), a foodstuff intermediate (for example a baking mix) or an auxiliary in foodstuff preparation (for example a baking powder), which contains an odorant precursor according to the invention, is heated such that it is exposed to temperatures of >50° C. (preferably >100° C., in particular >180° C.), in particular in the course of processes conventional in the preparation of foodstuffs, such as boiling, frying, microwaving or baking.

In addition to the precursor compound according to the invention, washing or cleaning agents or laundry post-treatment agents according to the invention preferably contain at least one, preferably a plurality of, active components, in particular components with a detergent, conditioning and/or cleaning action, advantageously selected from the group comprising anionic surfactants, cationic surfactants, amphoteric surfactants, nonionic surfactants, acidifying agents, alkalizing agents, anticrease compounds, antibacterial substances, antioxidants, antiredeposition agents, antistatic agents, builder substances (builders), bleaching agents, bleach activators, bleaching stabilizers, bleach catalysts, ironing aids, odorants, shrinkage prevention agents, electrolytes, enzymes, color protectants, colorants, dye transfer inhibitors, fluorescent agents, fungicides, germicides, odor-complexing substances, hydrotropes, rinse aids, complexing agents, preservatives, corrosion inhibitors, optical brighteners, pearlescent agents, pH adjusting agents, waterproofing and impregnation agents, polymers, antiswelling and antislip agents, foam inhibitors, phyllosilicates, dirt-repellent substances, silver protection agents, silicone oils, UV protection substances, viscosity regulators, thickeners, discoloration inhibitors, graying inhibitors, vitamins and/or finishing active substances.

The quantities of the further possible ingredients in the washing or cleaning agents or laundry post-treatment agents according to the invention are in each case determined on the basis of the intended purpose of the agent in question and a person skilled in the art is in principle familiar with the orders of magnitude of the quantities to be used of the optional ingredients or can find such details in the relevant specialist literature.

Depending on the intended purpose of the washing or cleaning agents or laundry post-treatment agents according to the invention, a higher or lower surfactant content will for example be selected. For example, the surfactant content of washing agents for example is conventionally between for example 5 and 50 wt. %, preferably between 10 and 30 wt. % and in particular between 15 and 25 wt. %, while cleaning agents for automatic dishwashing conventionally contain between for example 0.1 and 10 wt. %, preferably between 0.5 and 7.5 wt. % and in particular between 1 and 5 wt. % surfactants.

The washing or cleaning agents or laundry post-treatment agents according to the invention may preferably contain surfactants, in which in particular not only anionic surfactants, nonionic surfactants and mixtures thereof, but also cationic surfactants may be considered.

Optionally usable nonionic surfactants include the alkoxylates, in particular the ethoxylates and/or propoxylates, of saturated or mono- to polyunsaturated linear or branched-chain alcohols with 10 to 22 C atoms, preferably 12 to 18 C atoms. The degree of alkoxylation of the alcohols is here generally between 1 and 20, preferably between 3 and 10. They may be produced in known manner by reacting the corresponding alcohols with the corresponding alkylene oxides. Fatty alcohol derivatives are in particular suitable, although the branched-chain isomers thereof, in particular "oxo" alcohols, may be used to produce usable alkoxylates. The alkoxylates, in particular ethoxylates, of primary alcohols with linear, in particular dodecyl, tetradecyl, hexadecyl or octadecyl residues and mixtures thereof are accordingly usable. Corresponding alkoxylation products of alkylamines, vicinal diols and carboxamides which correspond to the stated alcohols with regard to the alkyl moiety, are moreover usable. The ethylene oxide and/or propylene oxide insertion products of fatty acid alkyl esters and fatty acid polyhydroxyamides may also be considered.

"Alkyl polyglycosides" suitable for optional incorporation into the agents according to the invention are compounds of the general formula $(G)_n$-$OR^8$, in which $R^8$ means an alkyl or alkenyl residue with 8 to 22 C atoms, G a glycose unit and n a number between 1 and 10. The glycoside component $(G)_n$ comprises oligomers or polymers prepared from naturally occurring aldose or ketose monomers, which in particular include glucose, mannose, fructose, galactose, talose, gulose, altrose, allose, idose, ribose, arabinose, xylose and lyxose. The oligomers consisting of such glycosidically linked monomers are characterized, apart from by the nature of the sugars contained therein, by the number thereof, the "degree of oligomerization". Since it has to be determined analytically, the degree of oligomerization n generally assumes fractional numerical values; these values are between 1 and 10, in the case of preferably used glycosides below a value of 1.5, in particular between 1.2 and 1.4. Glucose is the preferred monomer building block due to its ready availability. The alkyl or alkenyl moiety $R^8$ of the glycosides preferably likewise originates from readily available derivatives of renewable raw materials, in particular from fatty alcohols, although the branched-chain isomers thereof, in particular "oxo" alcohols, may be used to produce usable glycosides. Primary alcohols with linear octyl, decyl, dodecyl, tetradecyl, hexadecyl or octadecyl residues and mixtures thereof are accordingly in particular usable. Particularly preferred alkyl glycosides contain a coconut fatty alkyl residue, i.e. mixtures with substantially $R^8$=dodecyl and $R^8$=tetradecyl.

Nonionic surfactant is preferably optionally present in washing or cleaning agents according to the invention in quantities of 0.1 wt. % to 30 wt. %, in particular of 1 wt. % to 25 wt. %, wt. % relative to the entire washing or cleaning agent.

Instead of or in addition thereto, the washing or cleaning agents may contain further optional surfactants, preferably anionic surfactants.

Anionic surfactants of the sulfate or sulfonate type are preferably optionally present in quantities of preferably no more than 30 wt. %, in particular of 0.1 wt. % to 18 wt. %, in each case relative to the entire washing or cleaning agent. Anionic surfactants which may be mentioned as particularly suitable for use in the washing or cleaning agents according to the invention are alkyl and/or alkenyl sulfates with 8 to 22 C atoms which bear an alkali metal-, ammonium- or alkyl- or hydroxyalkyl-substituted ammonium ion as countercation. The derivatives of fatty alcohols with in particular 12 to 18 C atoms and the branched-chain analogs thereof, namely "oxo" alcohols, are preferred. The alkyl and alkenyl sulfates may be produced in known manner by reacting the corresponding alcohol component with a conventional sulfation reagent, in particular sulfur trioxide or chlorosulfonic acid, and subsequent neutralization with alkali metal-, ammonium- or alkyl- or hydroxyalkyl-substituted ammonium bases. Such alkyl and/or alkenyl sulfates are preferably optionally present in the washing or cleaning agents in quantities of 0.1 wt. % to 20 wt. %, in particular of 0.5 wt. % to 18 wt. %.

Usable surfactants of the sulfate type also include the sulfated alkoxylation products of the stated alcohols, namely "ether sulfates". Such ether sulfates preferably contain 2 to 30, in particular 4 to 10, ethylene glycol groups per molecule. Usable anionic surfactants of the sulfonate type include the α-sulfo esters obtainable by reacting fatty acid esters with sulfur trioxide and subsequent neutralization, in particular the sulfonation products derived from fatty acids with 8 to 22 C atoms, preferably 12 to 18 C atoms, and linear alcohols with 1 to 6 C atoms, preferably 1 to 4 C atoms, and the sulfofatty acids obtained from said sulfonation products by formal saponification.

Particularly preferred optionally usable anionic surfactants are alkylbenzenesulfonates, such as for example sodium dodecylbenzenesulfonate.

Anionic surfactant is preferably optionally present in washing or cleaning agents according to the invention in quantities of 0.1 wt. % to 30 wt. %, in particular of 1 wt. % to 25 wt. %, wt. % relative to the entire washing or cleaning agent.

Soaps may be considered as further optionally usable surfactant ingredients of the washing or cleaning agents, suitable soaps being saturated fatty acid soaps, such as the salts of lauric acid, myristic acid, palmitic acid or stearic acid, and soaps derived from natural fatty acid mixtures, for example coconut, palm kernel or tallow fatty acids. In particular, such soap mixtures which are preferred are those which are composed to an extent of 50 to 100 wt. % of saturated $C_{12}$-$C_{18}$ fatty acid soaps and to an extent of up to 50 wt. % of oleic acid soap. Soap is preferably optionally present in washing or cleaning agents according to the invention in quantities of 0.1 wt. % to 5 wt. %. In particular in liquid washing or cleaning agents, however, larger quantities of soap of up to 20 wt. % may optionally be present.

Cationic surfactants may also optionally be present in the washing or cleaning agents according to the invention, in particular in the laundry post-treatment agent according to the invention. Examples of cationic surfactants are quaternary ammonium compounds with preferably one or in particular two hydrophobic alkyl residues. Ester quats are particularly preferred, i.e. quaternary ammonium compounds with two hydrophobic residues, each of which contains an ester group as a "predetermined breaking point" to facilitate biodegradation. Preferably usable ester quats are methyl-N-(2-hydroxyethyl)-N,N-di(tallowacyloxyethyl)ammonium methosulfate, bis-(palmitoyloxyethyl)-hydroxyethylmethylammonium methosulfate, 1,2-bis-[tallowacyloxy]-3-trimethylammoniumpropane chloride, N,N-dimethyl-N,N-di(tallowacyloxyethyl)ammonium methosulfate or methyl-N,N-bis(stearoyloxyethyl)-N-(2-hydroxyethyl)ammonium methosulfate.

The cationic surfactants are preferably present in the agents according to the invention in quantities of 0.05 to 20 wt. %, relative to the total agent. Quantities of 0.1 to 5 wt. % are particularly preferred.

According to a preferred embodiment of the invention, surfactants are present in washing or cleaning agents according to the invention in a total quantity of preferably 5 wt. % to 50 wt. %, in particular of 8 wt. % to 30 wt. %. In particular in laundry post-treatment agents, surfactants are preferably used in an amount of up to 30 wt. %, in particular of 5 wt. % to 15 wt. %, said surfactant preferably comprising at least a proportion of cationic surfactants.

A washing or cleaning agent according to the invention may preferably contain at least one builder, preferably a water-soluble and/or water-insoluble, organic and/or inorganic builder. It is preferred to use water-soluble builders.

Water-soluble organic builder substances include polycarboxylic acids, in particular citric acid and saccharic acids, monomeric and polymeric aminopolycarboxylic acids, in particular methylglycinediacetic acid, nitrilotriacetic acid and ethylenediaminetetraacetic acid together with polyaspartic acid, polyphosphonic acids, in particular aminotris(methylenephosphonic acid), ethylenediaminetetrakis(methylenephosphonic acid) and 1-hydroxyethane-1,1-diphosphonic acid, polymeric hydroxyl compounds such as dextrin and polymeric (poly-)carboxylic acids, polymeric acrylic acids, methacrylic acids, maleic acids and copolymers thereof, which may also contain small proportions of polymerizable substances without carboxylic acid functionality incorporated by polymerization. Suitable, albeit less preferred, compounds of this class are copolymers of acrylic acid or methacrylic acid with vinyl ethers, such as vinyl methyl ethers, vinyl esters, ethylene, propylene and styrene, the acid fraction of which amounts to at least 50 wt. %.

Organic builder substances may, if desired, be present in the washing or cleaning agents according to the invention in quantities of up to 40 wt. %, in particular of up to 25 wt. % and preferably of 1 wt. % to 8 wt. %. Quantities close to the stated upper limit are preferably used in pasty or liquid, in particular hydrous, washing or cleaning agents according to the invention. Washing or cleaning agents according to the invention such as laundry post-treatment agents, such as for example rinse conditioners, may optionally contain no organic builder.

Water-soluble inorganic builder materials which may be considered are in particular alkali metal silicates and polyphosphates, preferably sodium triphosphate. Water-insoluble, water-dispersible inorganic builder materials which are optionally used in the washing or cleaning agents according to the invention are in particular crystalline or amorphous alkali metal aluminosilicates in quantities of for example up to 50 wt. %, preferably of no more than 40 wt. % and, in liquid agents, in particular from 1 wt. % to 5 wt. %. Among these, washing agent grade crystalline sodium aluminosilicates, in particular zeolite A, P and optionally X, are preferred. Quantities close to the stated upper limit are preferably optionally used in solid, particulate agents. Suitable substitutes or partial substitutes for the stated aluminosilicate are crystalline alkali metal silicates, which may be present alone or mixed with amorphous silicates. The alkali metal silicates usable as builders in the washing or cleaning agents according to the invention preferably have a molar ratio of alkali metal oxide to $SiO_2$ of below 0.95, in particular of 1:1.1 to 1:12 and may be in amorphous or crystalline form. Amorphous alkali metal silicates are preferred.

It is furthermore preferred for the purposes of a further preferred embodiment to use at most small quantities of water-insoluble builder materials (such as for example zeolite), for example in quantities of 0-5 wt. %, for example 0.1 to 2 wt. %, relative to the entire washing or cleaning agent.

Builder substances are preferably optionally present in the washing or cleaning agents according to the invention in quantities of up to 60 wt. %, in particular of 5 wt. % to 40 wt. %. Laundry post-treatment agents according to the invention, such as for example rinse conditioners, preferably contain no inorganic builder.

Optionally usable peroxy compounds which may in particular be considered are organic peracids or peracidic salts of organic acids, such as phthalimidopercaproic acid, perbenzoic acid or salts of diperdodecanedioic acid, hydrogen peroxide and inorganic salts, such as perborate, percarbonate and/or persilicate, which release hydrogen peroxide under the conditions of use. Where solid peroxy compounds are to be used, they may be used in the form of powders or granules, which may also in principle be encapsulated in known manner. Alkali metal percarbonate, alkali metal perborate monohydrate or, in particular in liquid agents, hydrogen peroxide in the form of aqueous solutions containing 3 wt. % to 10 wt. % hydrogen peroxide may particularly preferably be used. If a washing or cleaning agent according to the invention contains bleaching agents, in particular peroxy compounds, these are preferably present in quantities of up to 50 wt. %, in particular of 5 wt. % to 30 wt. %. It may be appropriate optionally to add small quantities of known bleaching agent stabilizers, such as for example phosphonates, borates or metaborates and metasilicates and magnesium salts such as magnesium sulfate.

Bleach activators which may optionally be used are compounds which, under perhydrolysis conditions, yield aliphatic peroxycarboxylic acids with preferably 1 to 10 C atoms, in particular 2 to 4 C atoms, and/or optionally substituted perbenzoic acid. Suitable substances are those which bear O- and/or N-acyl groups having the stated number of C atoms and/or optionally substituted benzoyl groups. Preferred compounds are polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate, 2,5-diacetoxy-2,5-dihydrofuran and enol ester and acetylated sorbitol and mannitol or mixtures thereof, acylated sugar derivatives, in particular pentaacetyl glucose (PAG), pentaacetyl fructose, tetraacetyl xylose and octaacetyl lactose and acetylated, optionally N-alkylated glucamine and gluconolactone, and/or N-acylated lactams, for example N-benzoyl caprolactam. Hydrophilically substituted acyl acetals and acyl lactams are likewise preferably used. Combinations of conventional bleach activators may also be used. Such bleach activators may optionally be present in conventional quantity ranges, preferably in quantities of 1 wt. % to 10 wt %, in particular 2 wt. % to 8 wt. %, relative to the entire agent.

Enzymes which are optionally usable in the washing or cleaning agents and may in particular be considered are those from the class of proteases, cutinases, amylases, pullulanases, hemicellulases, cellulases, lipases, oxidases and peroxidases and mixtures thereof. Enzymatic active substances which are particularly suitable are those obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia*. The optionally used enzymes may be adsorbed onto carrier substances and/or be embedded in encapsulating substances in order to protect them from premature inactivation They are preferably optionally present in the washing or cleaning agents according to the invention in quantities of up to 5 wt. %, in particular of 0.2 wt. % to 2 wt. %.

The washing or cleaning agents may optionally contain for example derivatives of diaminostilbene disulfonic acid or the alkali metal salts thereof as optical brighteners. Suitable compounds are, for example, salts of 4,4'-bis(2-anilino-4-morpholino-1,3,5-triazinyl-6-amino)stilbene 2,2'-disulfonic acid or compounds of similar structure which, instead of the morpholino group, bear a diethanolamino group, a methylamino group, an anilino group or a 2-methoxyethylamino group. Brighteners of the substituted diphenylstyryl type may furthermore be present, for example the alkali metal salts of 4,4'-bis(2-sulfostyryl)-diphenyl, 4,4'-bis(4-chloro-3-sulfostyryl)-diphenyl, or 4-(4-chlorostyryl)-4'-(2-sulfostyryl)-diphenyl. Mixtures of the above-stated brighteners may also be used.

Optionally usable foam inhibitors include, for example, organopolysiloxanes and mixtures thereof with microfine, optionally silanized silica as well as paraffin waxes and mixtures thereof with silanized silica or bis-fatty acid alkylenediamides. Mixtures of different foam inhibitors may also advantageously be used, for example mixtures of silicones, paraffins or waxes. The optional foam inhibitors, in particular foam inhibitors containing silicone and/or paraffin, are preferably bound to a granular carrier substance which is soluble or dispersible in water. Mixtures of paraffin waxes and bis-stearyl ethylenediamides are particularly preferred here.

The washing or cleaning agents may optionally also additionally contain components which have a positive impact on the removability of oil and grease from textiles by washing, namely soil-release active substances. This effect is particularly clear when a textile is soiled which has already previously been washed repeatedly with a washing agent which contains this oil and grease dissolving component. Preferred oil and grease dissolving components include, for example, nonionic cellulose ethers such as methylcellulose and methylhydroxypropylcellulose with a content of methoxy groups of 15 to 30 wt. % and of hydroxypropoxyl groups of 1 to 15 wt. %, in each case relative to the nonionic cellulose ethers, as well as the polymers known from the prior art of phthalic acid and/or terephthalic acid or of the derivatives thereof with monomeric and/or polymeric diols, in particular polymers prepared from ethylene terephthalates and/or polyethylene glycol terephthalates or anionically and/or nonionically modified derivatives of these.

The washing or cleaning agents may optionally also contain dye transfer inhibitors, preferably in quantities of 0.1 wt. % to 2 wt. %, in particular 0.1 wt. % to 1 wt. %, which in a preferred development of the invention are polymers of vinylpyrrolidone, vinylimidazole, vinylpyridine N-oxide or copolymers of these. Usable substances are not only polyvinylpyrrolidones, N-vinylimidazole/N-vinylpyrrolidone copolymers, polyvinyloxazolidones, copolymers based on vinyl monomers and carboxamides, polyesters and polyamides containing pyrrolidone groups, grafted polyamidoamines and polyethyleneimines, polymers with amide groups derived from secondary amines, polyamine N-oxide polymers, polyvinyl alcohols but also copolymers based on acrylamidoalkenylsulfonic acid.

Optionally usable graying inhibitors have the ability to keep dirt which has been dissolved from the textile fibers suspended in the liquor. Water-soluble colloids of a mainly organic nature are suitable for this purpose, for example starch, size, gelatin, salts of ether carboxylic acids or ether sulfonic acids of starch or cellulose or salts of acidic sulfuric acid esters of cellulose or starch. Water-soluble polyamides containing acidic groups are also suitable for this purpose. Derivatives of starch other than those stated above, for example aldehyde starches, may further be used. Cellulose ethers, such as carboxymethylcellulose (Na salt), methylcellulose, hydroxyalkylcellulose and mixed ethers, such as methylhydroxyethylcellulose, methylhydroxypropylcellulose, methylcarboxymethylcellulose and mixtures thereof, may preferably be used as optional graying inhibitors, for example in quantities of 0.1 to 5 wt. % relative to the washing or cleaning agent.

Organic solvents which are optionally usable in the washing or cleaning agents according to the invention, in particular if these are in liquid or pasty form, include alcohols with 1 to 4 C atoms, in particular methanol, ethanol, isopropanol and tert.-butanol, diols with 2 to 4 C atoms, in particular ethylene glycol and propylene glycol, and mixtures thereof and the ethers derivable from the stated classes of compounds. Such water-miscible solvents may be optionally present in the washing or cleaning agents according to the invention preferably in quantities of no more than 30 wt. %, in particular of 6 wt. % to 20 wt. %.

In order to establish a desired pH value which is not automatically obtained by mixing the remaining components, the washing or cleaning agents according to the invention may optionally contain acids, in particular citric acid, acetic acid, tartaric acid, malic acid, lactic acid, glycolic acid, succinic acid, glutaric acid and/or adipic acid, as well as mineral acids, in particular sulfuric acid, or bases, in particular ammonium or alkali metal hydroxides. Such pH regulators may optionally be present in the washing or cleaning agents according to the invention in quantities of preferably no more than 20 wt. %, in particular of 1.2 wt. % to 17 wt. %.

Solid agents according to the invention, such as in particular washing or cleaning agents, may be produced in a manner known in principle, for example by spray drying or granulation, with for example optional peroxy compound and optional bleach catalyst optionally being added subsequently. The odorant precursor used according to the invention is preferably introduced into the agent at the end of production, preferably by being sprayed on, in particular together with further odorants or with a perfume oil. Agents according to the invention, for example washing or cleaning agents, with an elevated bulk density, in particular in the range from 650 g/l to 950 g/l, may preferably be produced by a method comprising an extrusion step. Liquid agents according to the invention, for example washing or cleaning agents, may likewise be produced in a manner known per se, the odorant precursor used according to the invention preferably being introduced into the agent, for example washing or cleaning agent, at the end of production, in particular together with further odorants or with a perfume oil.

According to a preferred embodiment, the teaching according to the invention may be used to reduce the perfume content in the agents in question, such as for example washing or cleaning agents, such as in particular laundry post-treatment agents, since particularly efficient perfuming can be ensured by incorporating the odorant composition according to the invention, said perfuming being obtained as desired from targeted scent release and/or a long-lasting scent release.

A preferred washing or cleaning agent according to the invention is a solid, in particular pulverulent, washing agent which, in addition to odorant precursor compound according to the invention, may preferably contain components which are in particular selected from the following:
(a) anionic surfactants, such as preferably alkylbenzenesulfonate, alkyl sulfate, for example in quantities of preferably 5-30 wt. %

(b) nonionic surfactants, such as preferably fatty alcohol polyglycol ethers, alkyl polyglucoside, fatty acid glucamide, for example in quantities of preferably 0.5-15 wt. %

(c) builders, such as for example polycarboxylate, sodium citrate, in quantities of for example 0-70 wt. %, advantageously 5-60 wt. %, preferably 10-55 wt. %, in particular 15-40 wt. %, (d) alkalis, such as for example sodium carbonate, in quantities of for example 0-35 wt. % advantageously 1-30 wt. %, preferably 2-25 wt. %, in particular 5-20 wt. %, (e) bleaching agents, such as for example sodium perborate or sodium percarbonate, in quantities of for example 0-30 wt. % advantageously 5-25 wt. %, preferably 10-20 wt. %, (f) corrosion inhibitors, for example sodium silicate, in quantities of for example 0-10 wt. %, advantageously 1-6 wt. %, preferably 2-5 wt. %, in particular 3-4 wt. %, (g) stabilizers, for example phosphonates, advantageously 0-1 wt. %, (h) foam inhibitors, such as for example soap, silicone oils, paraffins, advantageously 0-4 wt. %, preferably 0.1-3 wt. %, in particular 0.2-1 wt. %, (i) enzymes, such as for example proteases, amylases, cellulases, lipases, advantageously 0-2 wt. %, preferably 0.2-1 wt. %, in particular 0.3-0.8 wt. %, (j) graying inhibitors, for example carboxymethylcellulose, advantageously 0-1 wt. %, (k) discoloration inhibitors, for example polyvinylpyrrolidone derivatives, for example 0-2 wt. %, (l) adjusting agents, for example sodium sulfate, advantageously 0-20 wt. %, (m) optical brighteners, for example stilbene derivative, biphenyl derivative, advantageously 0-0.4 wt. %, in particular 0.1-0.3 wt. %, (n) optionally further odorants, (o) optionally water, (p) optionally soap, (q) optionally bleach activators, (r) optionally cellulose derivatives, (s) optionally soil repellents, wt. % in each case relative to the entire agent.

In one particularly preferred embodiment, the washing or cleaning agent according to the invention is in solid, in particular particulate, form and, in addition to the precursor compound according to the invention, also contains 5 wt. % to 55 wt. % builders, 2.5 wt. % to 20 wt. % anionic surfactant, 1 wt. % to 20 wt. % nonionic surfactant, 1 wt. % to 25 wt. % bleaching agent, 0.5 wt. % to 8 wt. % bleach activator and 0.1 wt. % to 40 wt. % adjusting agent, in particular alkali metal sulfate, and up to 2 wt. %, in particular 0.4 wt. % to 1.2 wt. % enzyme, preferably enzyme formulated in particulate form, in particular protease, lipase, amylase, cellulase and/or oxidoreductase. This embodiment may optionally also contain neither bleaching agent nor bleach activator.

In another preferred embodiment of the invention, the washing or cleaning agent according to the invention is in liquid or cleaning agents have water contents of for example 10-95 wt. %, preferably 20-80 wt. % and in particular 30-70 wt. %, relative to the entire agent. In the case of liquid concentrates, the water content may also be particularly low, for example amounting to ≤30 wt. %, preferably ≤20 wt. %, in particular ≤15 wt. %, such as for example 0.1 to 10 wt. %, wt. % in each case relative to the entire agent. The liquid agents may also contain nonaqueous solvents.

A preferred washing or cleaning agent according to the invention is a liquid, in particular gel form, washing agent which, in addition to odorant precursor compound according to the invention, may preferably contain components which are preferably selected from the following:

anionic surfactants, such as preferably alkylbenzenesulfonate, alkyl sulfate, for example in quantities of preferably 5-40 wt. % nonionic surfactants, such as preferably fatty alcohol polyglycol ether, alkyl polyglucoside, fatty acid glucamide, for example in quantities of preferably 0.5-25 wt. % builders, such as for example polycarboxylate, sodium citrate, advantageously 0-25 wt. %, preferably 0.01-10 wt. %, in particular 0.1-5 wt. %, foam inhibitors, for example silicone oils, paraffins, in quantities of for example 0-10 wt. %, advantageously 0.1-4 wt. %, preferably 0.2-2 wt. %, in particular 1-3 wt. %, enzymes, for example proteases, amylases, cellulases, lipases, in quantities of for example 0-3 wt. %, advantageously 0.1-2 wt. %, preferably 0.2-1 wt. %, in particular 0.3-0.8 wt. %, optical brighteners, for example stilbene derivative, biphenyl derivative, in quantities of for example 0-1 wt. %, advantageously 0.1-0.3 wt. %, in particular 0.1-0.4 wt. %, optionally further odorants, water optionally soap, in quantities of for example 0-25 wt. %, advantageously 1-20 wt. %, preferably 2-15 wt. %, in particular 5-10 wt. %, optionally solvents (preferably alcohol), advantageously 0-25 wt. %, preferably 1-20 wt. %, in particular 2-15 wt. %, wt. % in each case relative to the entire agent.

A particularly preferred liquid washing or cleaning agent here contains, in addition to the odorant precursor compound according to the invention, at least anionic surfactants in quantities of 0.5 wt. % to 20 wt. %, nonionic surfactants in quantities of 1 wt. % to 25 wt. %, builders in quantities of 1 to 25 wt. %, enzymes and water.

A further preferred washing or cleaning agent according to the invention is a liquid rinse conditioner which, in addition to the odorant precursor compound according to the invention, may preferably contain components which are selected from the following:

cationic surfactants, such as in particular ester quats, for example in quantities of 5-30 wt. %, cosurfactants, such as in particular glycerol monostearate, stearic acid, fatty alcohols and/or fatty alcohol ethoxylates, for example in quantities of 0-5 wt. %, preferably 0.1-4 wt. %, emulsifiers, such as in particular fatty amine ethoxylates, for example in quantities of 0-4 wt. %, preferably 0.1-3 wt. %, optionally further odorants, optionally colorants, preferably in the ppm range, solvents, such as in particular water, for example in quantities of 60-90 wt. %, wt. % in each case relative to the entire agent.

EXAMPLES

Example 1

Trans-Pinocarvyl Oxyacetic Acid Methyl Ester

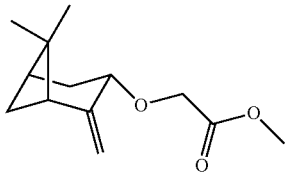 [SMILES: C=C1C(OCC(=O)OC)CC2CC1C2(C)C]

Structure:

Synthesis: 2 equivalents of NaH were suspended in dry THF in an argon-filled flask. 1 equivalent of trans-pinocarveol in dry THF was then added and stirred for 40 minutes. 1.5 equivalents of methylesther 2-bromoacetate were then added slowly. Once the reaction was complete, the batch was combined with a little water and the aqueous phase extracted twice with ethyl acetate. The organic phases were washed with $Na_2SO_3$ and NaCl solution and dried with $MgSO_4$. Excess solvent was removed and the crude product purified by column chromatography.

Thermally Induced Release of α-Pinene:

a) Trans-pinocarvyl oxyacetic acid methyl ester was dissolved in N-methyl-2-pyrrolidone and heated to 200° C. for 2 h. As a result, 50% of the trans-pinocarvyl oxyacetic acid methyl ester was converted to α-pinene, which could be detected by GC-MS.

b) The trans-pinocarvyl oxyacetic acid methyl ester was incorporated into an ironing aid containing castor oil ethoxylate and essential orange oil. The ironing aid was sprayed onto a cotton cloth which was then ironed at a temperature of 220° C. An odor of turpentine, which is characteristic of α-pinene, could be perceived as a consequence.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An odorant composition, containing an odorant precursor, which is an allyl ether of the formula (I), $$R^1R^2C=CR^3-CR^4R^5-O-CHR^6R^7 \qquad (I),$$

in which the residues $R^1$, $R^2$, $R^3$, $R^4$, $R^5$, $R^6$ and $R^7$ mutually independently in each case denote H or a hydrocarbon residue that can be acyclic or cyclic, substituted or unsubstituted, branched or unbranched, as well as saturated or unsaturated, and in which individual residues $R^1$, $R^2$, $R^3$, $R^4$, $R^5$, $R^6$, $R^7$ can form a ring system with one another, wherein $R^1$, $R^2$, $R^3$, $R^4$ and $R^5$ denote residues that, in a compound of the general formula (II)

$$R^1R^2CH-CR^3=CR^4R^5 \qquad (II),$$

give rise to an odorant,
wherein $R^6$ and $R^7$ denote residues that, in a compound of the general formula (III)

$$R^6R^7C=O \qquad (III),$$

give rise to an odorant,
and wherein the compound of the general formula (III) is selected from adoxal (2,6,10-trimethyl-9-undecenal), anisaldehyde (4-methoxybenzaldehyde), cymal (3-(4-isopropylphenyl)-2-methylpropanal), ethylvanillin, florhydral (3-(3-isopropylphenyl)butanal), helional (3-(3,4-methylenedioxyphenyl)-2-methylprop anal), heliotropin, hydroxycitronellal, lauraldehyde, lyral (3- and 4-(4-hydroxy-4-methylpentyl)-3-cyclohexene-1-carboxaldehyde), methylnonyl-acetaldehyde, lilial (3-(4-tert.-butylphenyl)-2-methylpropanal), phenylacetaldehyde, undecylenealdehyde, vanillin, 2,6,10-trimethyl-9-undecenal, 3-dodecen-1-al, alpha-n-amylcinnamaldehyde, melonal(2,6-dimethyl-5-heptenal), 2,4-dimethyl-3-cyclohexene-1-carboxaldehyde (triplal), benzaldehyde, 3-(4-tert.-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, 2,6-dimethyl-5-heptenal, 4-(tricyclo[5.2.1.0(2,6)]-decylidene-8)-butanal, octahydro-4,7-methane-1H-indenecarboxaldehyde, 3-ethoxy-4-hydroxybenzaldehyde, para-ethyl-alpha,alpha-dimethylhydrocinnamaldehyde, alpha-methyl-3,4-(methylenedioxy)-hydro-cinnamaldehyde, 3,4-methylenedioxybenzaldehyde, alpha-n-hexyl-cinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexane-3-carboxaldehyde, 4-(4-hydroxy-4-methylpentyl)-3-cylohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert.-butyl) propanal, dihydrocinnamaldehyde, 1-methyl-4-(4-methyl-3-pentenyl)-3-cyclohexene-1-carboxaldehyde, 5- or 6-methoxyhexahydro-4,7-methanindane-1- or -2-carboxaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxaldehyde, 7-hydroxy-3,7-dimethyloctanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanindane-1-carboxaldehyde, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]hept-5-ene-2-carbaldehyde, 9-decenal, 3-methyl-5-phenyl-1-pentanal, methylnonylacetaldehyde, hexanal and trans-2-hexenal.

2. The composition according to claim 1 wherein the composition contains further odorants.

3. A washing or cleaning agent containing an odorant composition according to claim 1 in quantities between 0.0001 and 10 wt. % relative to the entire agent.

4. A textile fragrancing method, wherein an odorant composition according to claim 1 is applied onto a textile and the surface of the textile is thereafter exposed to temperatures of ≥50° C.

5. An aromatization method in foodstuff preparation, wherein a foodstuff, a foodstuff precursor or a foodstuff preparation auxiliary that in each case contains an odorant composition according to claim 1 is heated such that it is exposed to temperatures of >50° C. in the course of conventional food preparation procedures such as boiling, frying, microwaving or baking.

6. An odorant composition, containing an odorant precursor, which is an allyl ether of the formula (I), $$R^1R^2C=CR^3-CR^4R^5-O-CHR^6R^7 \qquad (I),$$

in which the residues $R^1$, $R^2$, $R^3$, $R^4$, $R^5$, $R^6$ and $R^7$ mutually independently in each case denote H or a hydrocarbon residue that can be acyclic or cyclic, substituted or unsubstituted, branched or unbranched, as well as saturated or unsaturated, and in which individual residues $R^1$, $R^2$, $R^3$, $R^4$, $R^5$, $R^6$, $R^7$ can form a ring system with one another, wherein $R^1$, $R^2$, $R^3$, $R^4$ and $R^5$ denote residues that, in a compound of the general formula (II)

$$R^1R^2CH-CR^3=CR^4R^5 \qquad (II),$$

give rise to an odorant, wherein the alkene according to formula (II) is selected from the group consisting of limonene, α-phellandrene, β-phellandrene, α-pinene, β-pinene, camphene, caryophyllene, longifolene, ocimene; α-terpinene, β-terpinene, γ-terpinene, α-terpineol, δ-terpineol, γ-terpineol, β-terpineol, α-citronellol, β-citronellol, α-citronellal, β-citronellal, linalool, dihydromyrcenol, geraniol, santalol, hasmigone, carvone, 2-carene, 3-carene, 4-carene, elemol and curcumene, and/or wherein $R^6$ and $R^7$ denote residues that, in a compound of the general formula (III)

$$R^6R^7C=O \qquad (III),$$

give rise to an odorant.

* * * * *